US010213265B2

United States Patent
Yanagihara et al.

(10) Patent No.: US 10,213,265 B2
(45) Date of Patent: Feb. 26, 2019

(54) MANIPULATOR AND MANIPULATOR SYSTEM

(71) Applicant: OLYMPUS CORPORATION, Tokyo (JP)

(72) Inventors: Masaru Yanagihara, Tokyo (JP); Kosuke Kishi, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/616,341

(22) Filed: Jun. 7, 2017

(65) Prior Publication Data

US 2017/0265955 A1 Sep. 21, 2017

Related U.S. Application Data

(63) Continuation of application No. PCT/JP2016/050675, filed on Jan. 12, 2016.

(30) Foreign Application Priority Data

Feb. 19, 2015 (JP) .................................. 2015-030789

(51) Int. Cl.
*A61B 1/00* (2006.01)
*A61B 34/00* (2016.01)
(Continued)

(52) U.S. Cl.
CPC .......... *A61B 34/71* (2016.02); *A61B 1/00009* (2013.01); *A61B 1/0016* (2013.01);
(Continued)

(58) Field of Classification Search
CPC ... A61B 34/71; A61B 34/37; A61B 2034/301; A61B 1/0052; A61B 1/0057;
(Continued)

(56) References Cited

U.S. PATENT DOCUMENTS 6,702,737 B2 * 3/2004 Hino .................... A61B 1/0052
600/146
2007/0232858 A1 * 10/2007 Macnamara ......... A61B 1/0052
600/149

(Continued)

FOREIGN PATENT DOCUMENTS

EP 2 599 431 A1 6/2013
JP 2000-79586 A 3/2000
(Continued)

OTHER PUBLICATIONS

International Search Report dated Feb. 16, 2016 issued in PCT/JP2016/050675.
(Continued)

*Primary Examiner* — Timothy J Neal
(74) *Attorney, Agent, or Firm* — Scully, Scott, Murphy & Presser, P.C.

(57) ABSTRACT

A manipulator and a manipulator system adjust the initial tension easily yet unerringly during assembling. The manipulator includes a main unit, an elongated portion that extends from the main unit, a distal end that is connected to the elongated portion, a wire for transmission of power for putting the distal end into actuation, a drive unit for generation of power to the wire, a rotary unit which is located in the main unit, around which the wire is wound and which is rotated by the drive unit, and an elastic unit for connecting the wire to the rotary unit.

9 Claims, 11 Drawing Sheets

(51) Int. Cl.
  *A61B 34/37* (2016.01)
  *A61B 1/005* (2006.01)
  *A61B 1/018* (2006.01)
  *B25J 9/10* (2006.01)
  *A61B 34/30* (2016.01)

(52) U.S. Cl.
  CPC ........ *A61B 1/00045* (2013.01); *A61B 1/0052* (2013.01); *A61B 1/0057* (2013.01); *A61B 1/018* (2013.01); *A61B 34/37* (2016.02); *B25J 9/104* (2013.01); *A61B 1/00* (2013.01); *A61B 2034/301* (2016.02); *A61B 2034/306* (2016.02)

(58) Field of Classification Search
  CPC ..... A61B 1/0016; A61B 1/018; A61B 1/0009; A61B 1/00045
  See application file for complete search history.

(56) References Cited

U.S. PATENT DOCUMENTS

| | | |
|---|---|---|
| 2010/0082041 A1 | 4/2010 | Prisco |
| 2010/0331820 A1 | 12/2010 | Prisco et al. |
| 2012/0221146 A1 | 8/2012 | Zhang et al. |
| 2014/0107665 A1 | 4/2014 | Shellenberger et al. |
| 2014/0121462 A1* | 5/2014 | Okamoto ............. A61B 1/0052 600/149 |
| 2014/0128849 A1 | 5/2014 | Au et al. |
| 2016/0213224 A1 | 7/2016 | Hatakeyama et al. |

FOREIGN PATENT DOCUMENTS

| | | |
|---|---|---|
| JP | 2006-250296 A | 9/2006 |
| JP | 2007-319954 A | 12/2007 |
| JP | 2012-531943 A | 12/2012 |
| JP | 2015-024008 A | 2/2015 |
| WO | 2008/046030 A2 | 4/2008 |
| WO | WO 2011/059015 A1 | 5/2011 |

OTHER PUBLICATIONS

Japanese Office Action dated Nov. 8, 2016 received in JP Application No. 2016-546123.
Extended European Supplementary Search Report dated Oct. 11, 2018 received in European Patent Application No. 16 75 2159.0.
Chinese Office Action dated Dec. 3, 2018 received in Chinese Patent Application No. 201680004096.6.

* cited by examiner

MANIPULATOR AND MANIPULATOR SYSTEM

CROSS-REFERENCE TO RELATED APPLICATIONS

This application is a continuation claiming priority on the basis of Japan Patent Application No. 2015-030789 applied in Japan on Feb. 19, 2015 and based on PCT/JP2016/050675 filed on Jan. 12, 2016. The contents of both the PCT application and the Japan Application are incorporated herein by reference.

BACKGROUND OF THE INVENTION AND RELATED ART STATEMENT

The present invention relates to a manipulator having a distal end bent by bending a joint assembly for various treatments or the like as well as a manipulator system.

There has been a manipulator typically used wherein a treatment tool is inserted through the body cavity of a patient so that the distal end of the treatment tool is pulled and bent as by way of a wire for the purpose of viewing or otherwise treating the internal organs in it. Often for surgical operations, plural treatment tools such as an endoscope for viewing, forceps for taking grasp of a tissue or an electric scalpel for excising off tissues are inserted through the body cavity.

US2014/0128849A discloses a treatment tool having a bendable joint assembly at its distal end wherein a spring is used to keep tension thereby making tensions of a pair of wires equal.

SUMMARY OF INVENTION

According to one embodiment, a manipulator includes:
a drive unit for generating driving power,
a rotary unit including a shaft member that is rotated by the driving power and a disc member that is mounted on an outer periphery of the shaft member and has a peripheral wall,
a wire that has one end and the other end, is wound along and around the peripheral wall, and is pulled by rotation of the rotary unit,
an actuator that is connected to one end of the wire and put into actuation as the wire is pulled,
an elastic unit that is located along an outer peripheral surface of the peripheral wall, has one end and the other end, and is connected at the one end to the other end of the wire, and
a lock portion for locking the other end of the elastic unit to the rotary unit.

DESCRIPTION OF EMBODIMENTS

Some embodiments will now be explained.

Figure 1:
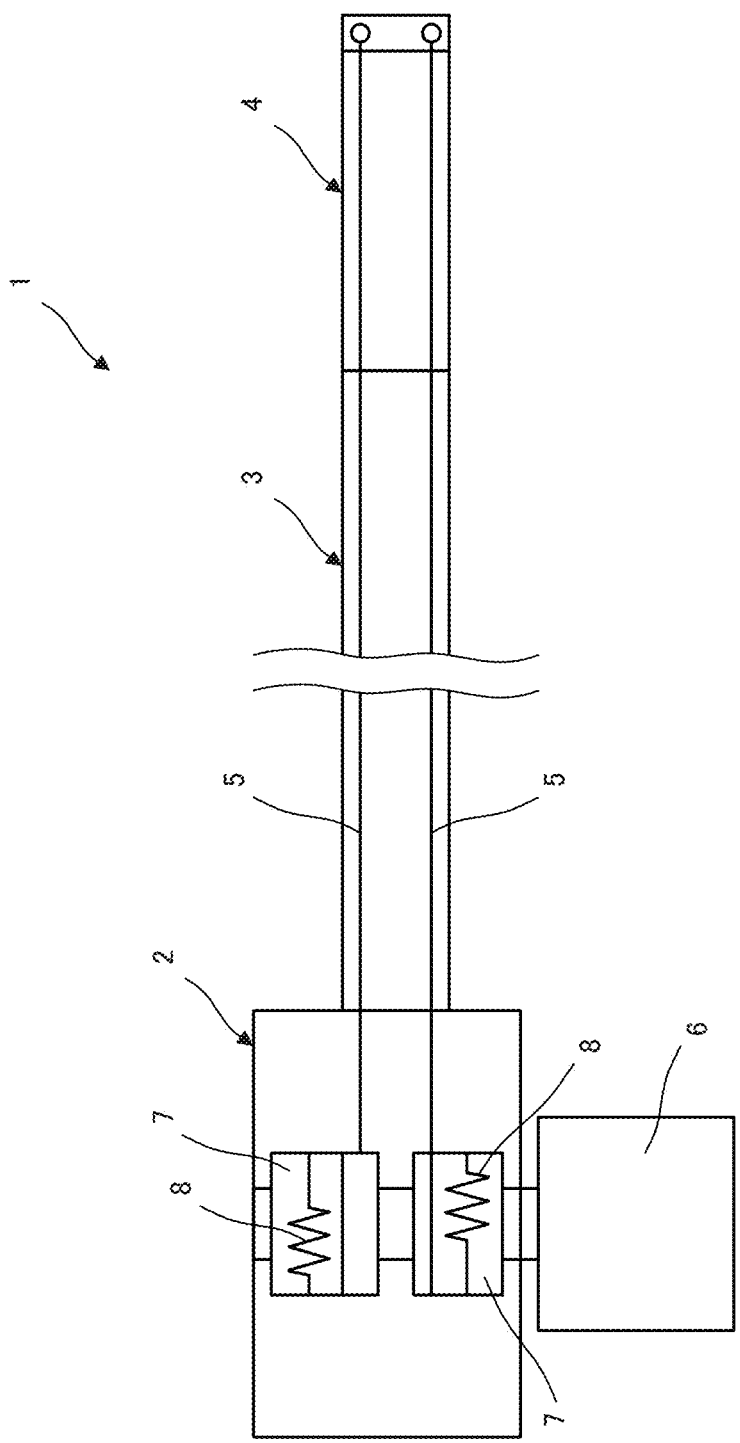
FIG. 1 illustrates the manipulator according to one embodiment.

FIG. 1 shows a manipulator 1 according to the embodiment described here.

The manipulator 1 described here includes a main unit 2, an elongated portion 3 extending from the main unit 2, a distal end 4 connected to the elongated member 3, a wire 5 for transmission of power adapted to put the distal end 4 into actuation, a drive unit 6 adapted to generate power to the wire 5, a rotary unit 7 around which the wire 5 is wound and which is rotated by the drive unit 6, and an elastic unit 8 adapted to make a connection between the wire 5 and the rotary unit 7.

The main unit 2 is a case-like portion for housing the rotary unit 7 that is rotated by the drive unit 6. The elongated portion 3 extends from the main unit 2. At the distal end of the elongated portion 3 there is the distal end 4 mounted that is capable of bending or flexing with respect to the elongated portion 3. The wire 5 is provided on one end side with the distal end 4 for insertion through the elongated portion 3, and wound on other end side around a portion of the rotary unit 7 for fixation to the rotary unit 7 by way of the elastic unit 8.

Figure 2:
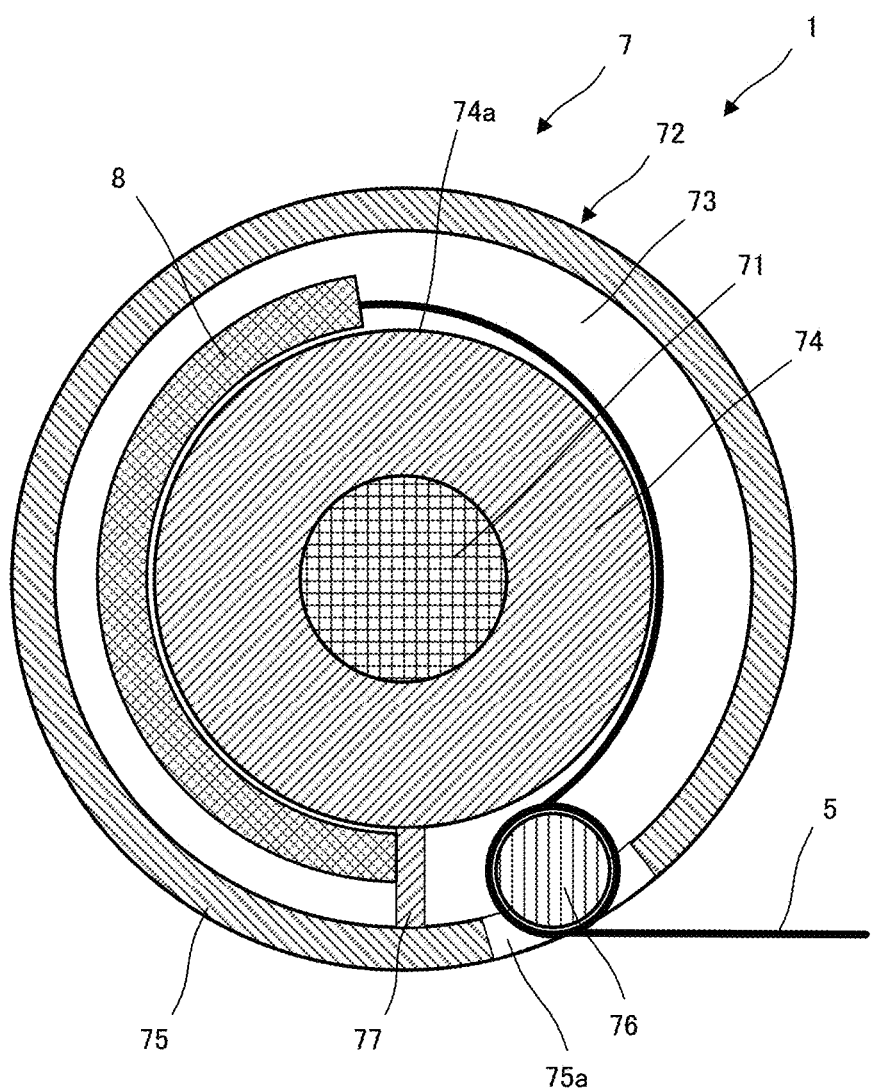
FIG. 2 is illustrative of one example of the rotary unit in the manipulator according to the first embodiment.

FIG. 2 is illustrative of one example of the rotary unit 7 in the manipulator 1 according to the first embodiment.

The rotary unit 7 includes a shaft member 71 that is rotated by the drive unit 6, and a disc member 72 mounted on the outer circumference of the shaft member 71. The shaft member 71 and disc member 72 are integrally rotated by the power of the drive unit 6. Note here that the shaft member 71 and disc member 72 may be formed of a single material as one integral piece, and that the disc member 72 may be directly attached to the output shaft of the drive unit 6 or the like.

The disc member 72 includes a plate portion 73, an inner peripheral wall 74 standing upright on the inner peripheral side of the plate portion 73, an outer peripheral wall 75 standing upright on the outer peripheral side of the plate portion 73, a columnar projection 76 that is at least partially mounted on the plate portion 73, and a lock portion 77 that fixes the terminal end of the elastic unit 8 in place. Note here that the projection 76 may be provided in such a way as to include a gap 75a formed in a portion of the outer peripheral wall 75.

Referring to the rotary unit 7 in the manipulator 1 according to the first embodiment, the wire 5 is inserted from the gap 75a to the inner peripheral side of the outer peripheral wall 75, then wound around the projection 76, and then located along the outer peripheral surface 74a of the inner peripheral wall 74. The wire 5 is mounted at its end on one end of the elastic unit 8. The elastic unit 8 is located along the outer peripheral surface 74a of the inner peripheral wall 74, and locked at the other end to the lock portion 77 formed on the plate portion 73 between the inner peripheral wall 74 and the outer peripheral wall 75.

Referring to such manipulator 1, as the drive unit 6 is driven for transmission of power to the rotary unit 7, it causes rotation of the shaft member 71 and disc member 72 of the rotary unit 7. As the disc member 72 is rotated to pull the wire 5, it allows the portion of the wire 5 on the distal end 4 side to be pulled by the projection 76 because the portion of the wire 5 wound around the projection 76 has an increased static friction. Thus, the tension applied on the elastic unit 8 remains invariable. As the disc member 72 rotated to let go of the wire 5, it causes a slack in the wire 5 to be absorbed by the elastic unit 8. It is thus possible to adjust the initial tension of the wire 5 easily yet unerringly.

Figure 3:
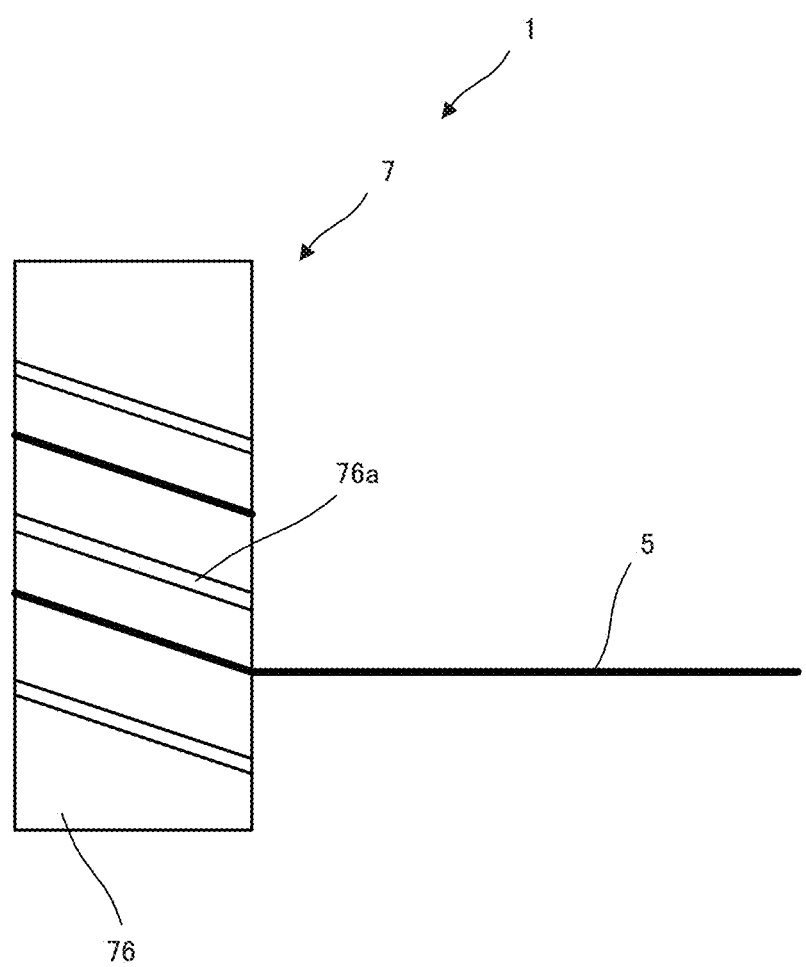
FIG. 3 illustrates another example of the wire-wound portion in the manipulator according to first embodiment.

FIG. 3 is illustrative of another example of the projection 76 in the manipulator 1 according to the first embodiment.

As shown in FIG. 3, the projection 76 may be provided with a guide 76a for guidance of the wire. The guide 76a is provided in such a way as to prevent the wire wound around the projection 76 from interference with itself. For instance, the guide 76a may be defined by such a partition wall as shown in FIG. 3 or, alternatively, a projection and depression not shown. Thus, providing the projection 76 with the guide 76a makes sure smooth actuation of the wire 5.

Figure 4:
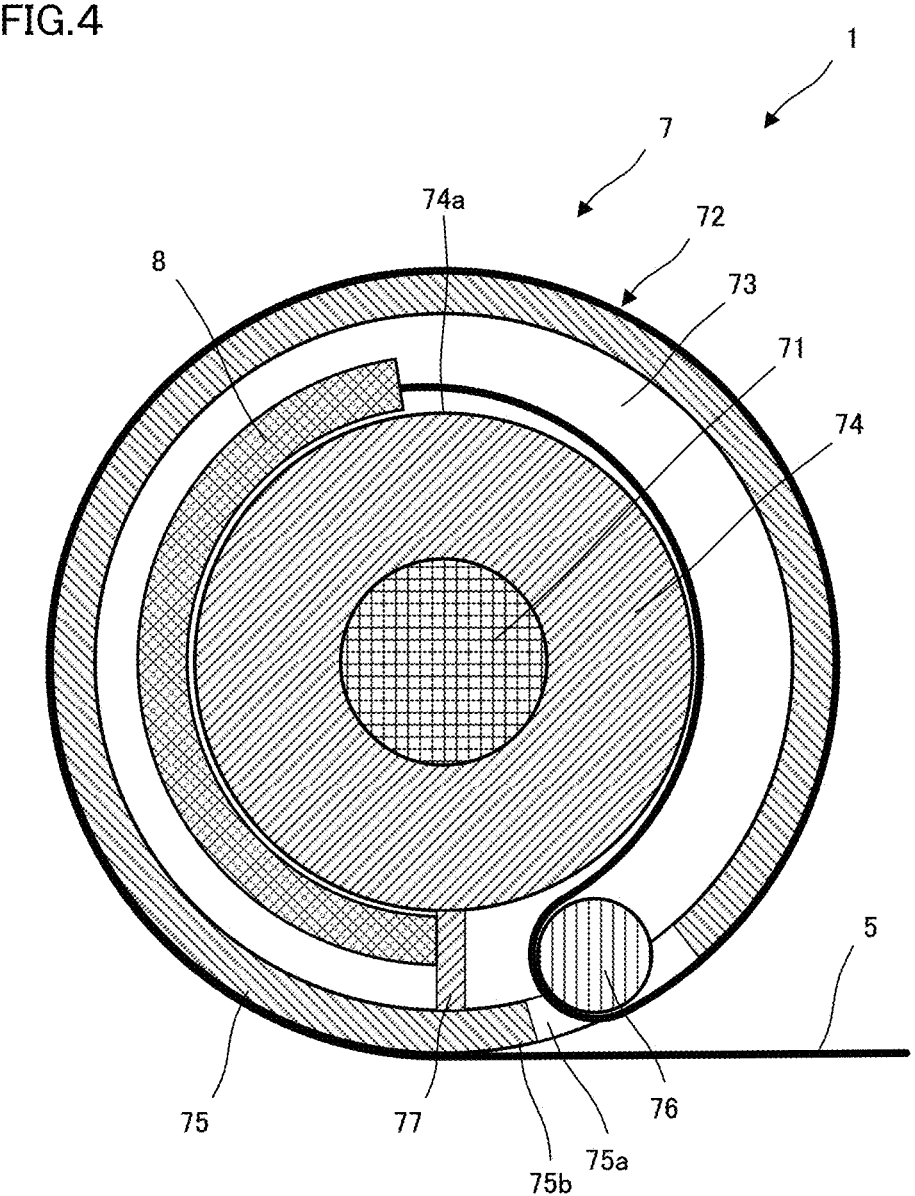
FIG. 4 illustrates another example of the rotary unit in the manipulator according to the first embodiment.

FIG. 4 is illustrative of another example of the rotary unit 7 in the manipulator 1 according to the first embodiment.

The example of FIG. 4 has a structure of winding the wire 5 around the outer peripheral surface 75b of the outer peripheral wall 75 of the rotary unit 7 in the manipulator 1.

Referring to the rotary unit 7 in the manipulator 1 of FIG. 4, the wire 5 is wound around the outer peripheral surface 75b of the outer peripheral wall 75, then inserted from the gap 75a to the inner peripheral side of the outer peripheral wall 75, then wound around a portion of the projection 76, and then located along the outer peripheral surface 74a of the inner peripheral wall 74. The end of the wire 5 is attached to one end of the elastic unit 8. The elastic unit 8 is located along the outer peripheral surface 74a of the inner peripheral wall 74, and locked at the other end to the lock portion 77 formed on the plate portion 73 between the inner peripheral wall 74 and the outer peripheral wall 75.

In such configuration, as the disc member 72 is rotated to pull the wire 5, it causes the portion of the wire 5 on the distal end 4 side to be pulled by the outer peripheral wall 75 because the portion of the wire 5 wound around the outer peripheral wall 75 has an increased static friction. Thus, the tension applied on the elastic unit 8 remains invariable. As the disc member 72 is rotated to let go of the wire 5, it causes a slack in the wire 5 to be absorbed by the elastic unit 8 so that the initial tension of the wire 5 can be adjusted easily yet unerringly.

Figure 5A:
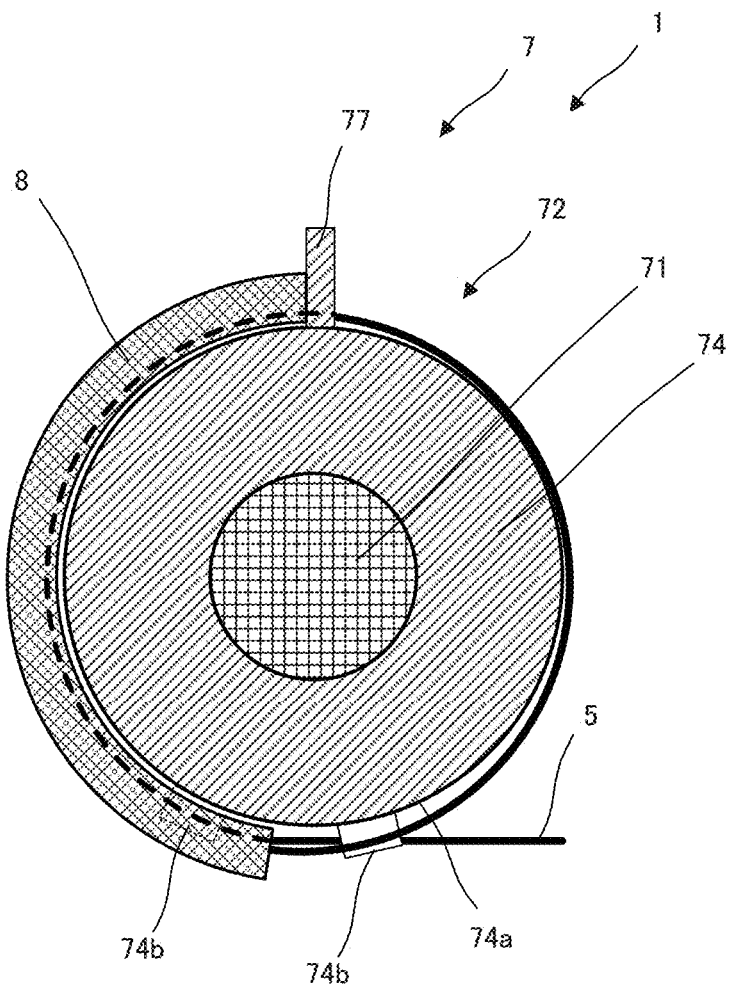
FIGS. 5A and 5B illustrate a portion of the rotary unit in the manipulator according to the second embodiment.
Figure 5B:
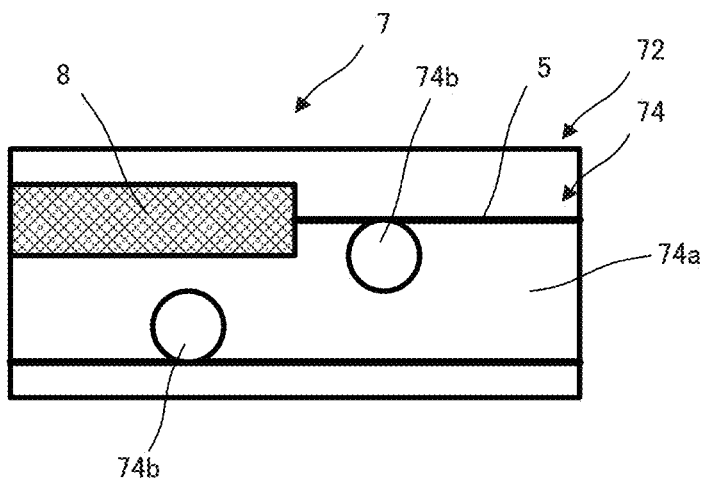

FIGS. 5A and 5B are illustrative of a portion of the rotary unit 7 in the manipulator 1 according to the second embodiment: FIG. 5A is a plan view of a portion of the rotary unit 7 and FIG. 5B is a side view of a portion of the rotary unit 7.

The example of FIGS. 5A and 5B have a structure of dispensing with the outer peripheral wall 75 of the rotary unit 7 in the manipulator 1 and instead winding the wire 5 around the outer peripheral surface 74a of the inner peripheral wall 74. The inner peripheral wall 74 is provided with guides 74b for guidance of the wire 5. The guides 74b are provided in positions where the wire 5 is vertically placed on itself and positions where the wire 5 and elastic unit 8 are vertically placed one upon another. The provision of the guides 74b ensures that the wire 5 is provided in such a way as to prevent interference with itself, and the wire 5 and elastic unit 8 are provided in such a way as to prevent them from interference with one another, allowing for smooth actuation. The guides 74b may be defined by such projections as shown in FIGS. 5A and 5B or, alternatively, partition walls or like structures. Thus, the structure of winding the wire 5 around the outer peripheral surface 74a of the inner peripheral wall 74 of the rotary unit 7 enables the wire 5 to be put into smooth actuation, and has a merit of cutting cost down because of a structural simplification of the rotary unit 7.

Figure 6A:
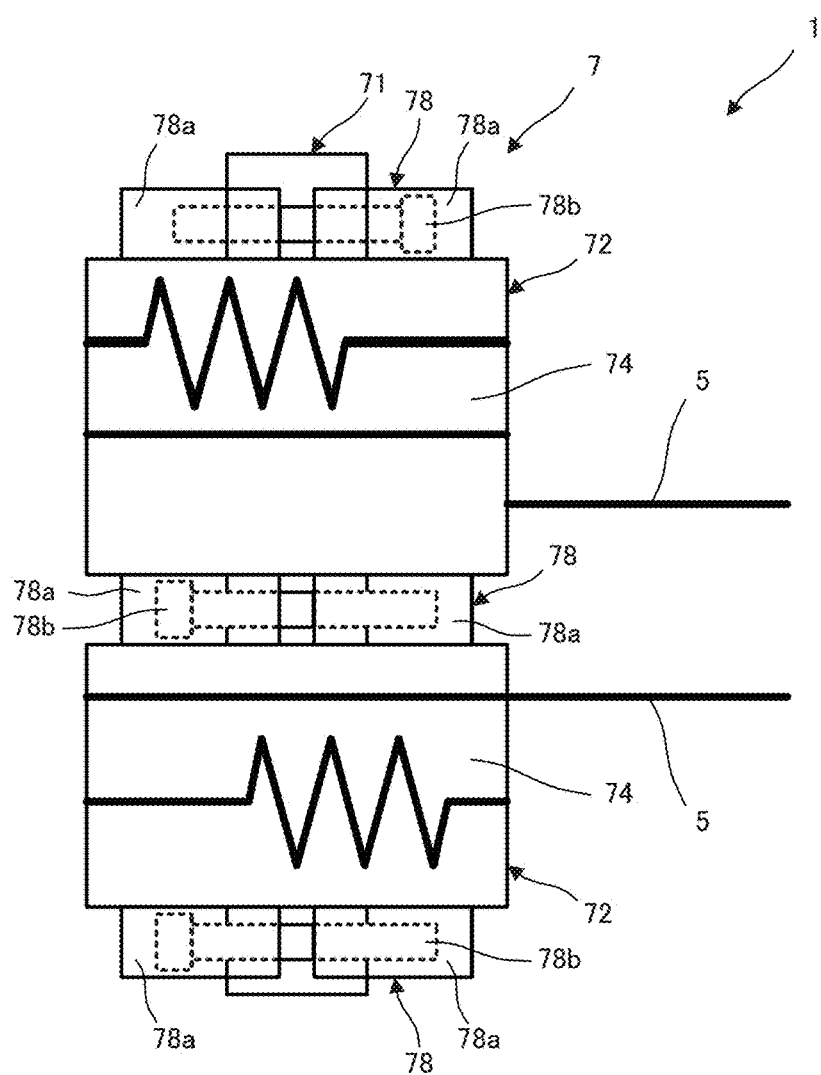
FIGS. 6A and 6B show the mounting structure of the rotary unit in the manipulator described here.
Figure 6B:
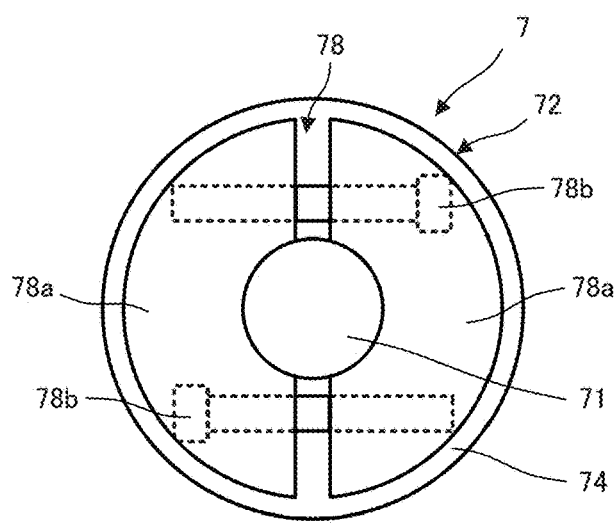

FIGS. 6A and 6B are illustrative of one mounting structure for the rotary unit 7 in the manipulator 1 according to the embodiment described here: FIGS. 6A and 6B are a side view and a plan view, respectively, of the rotary unit 7 having the disc member 72 mounted on the shaft member 71.

The disc member 72 is supported by a support portion 78 to the shaft member 71. The support portion 78 includes a two-split member 78a and a bolt 78b. The two-split member 78a looks as if an annular member were split into two with the shaft member 71 as center. The two-split member 78a is then coupled together by two bolts 78b between which the shaft member 71 is held. Preferably, the support portion 78 should support the disc member 72 from above and below in a sandwiched manner. Use of such support portion 78 makes it possible to support the disc member 72 unerringly.

It is here to be noted that at least a portion of the disc member 72 may be integral with the shaft member 71 without recourse to the support portion 78. Integral formation of the disc member 72 with the shaft member 71 makes it possible to cut down a parts count and cost.

Figure 7A:
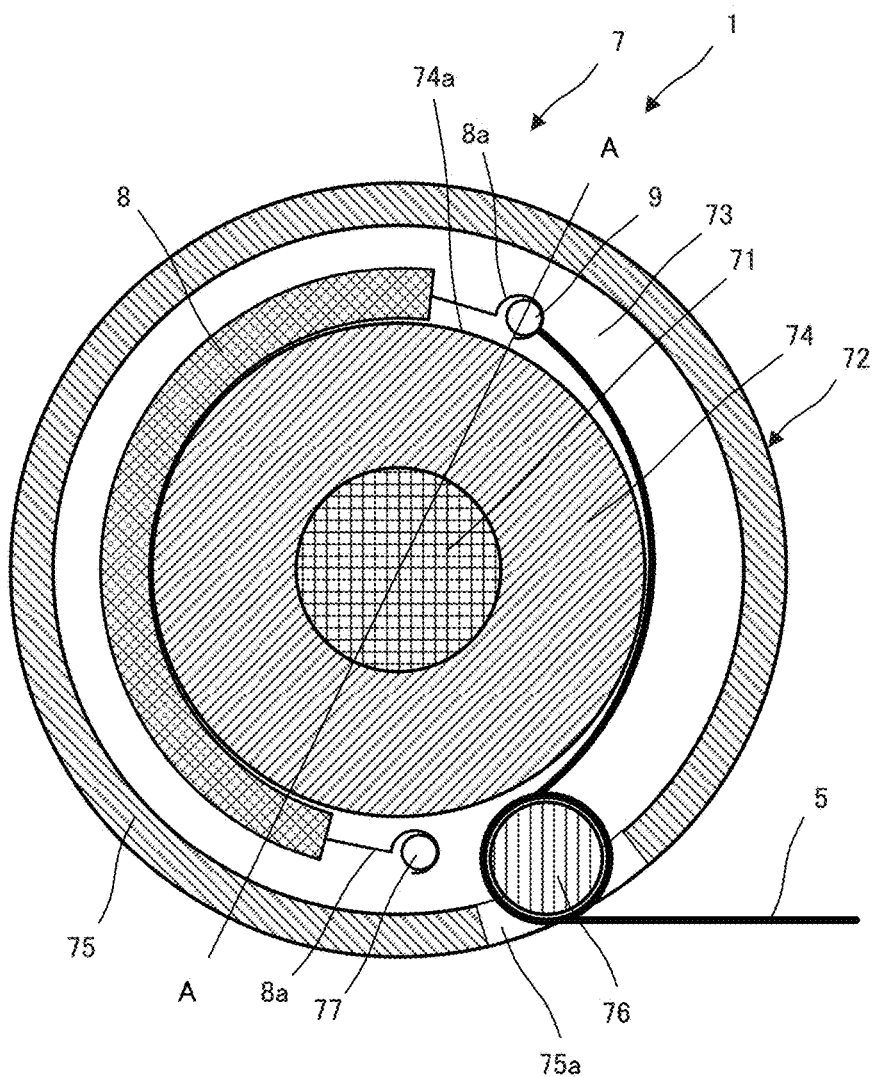
FIGS. 7A and 7B illustrate one example of how to mount the wire on the elastic unit in the manipulator according to the embodiment described here.
Figure 7B:
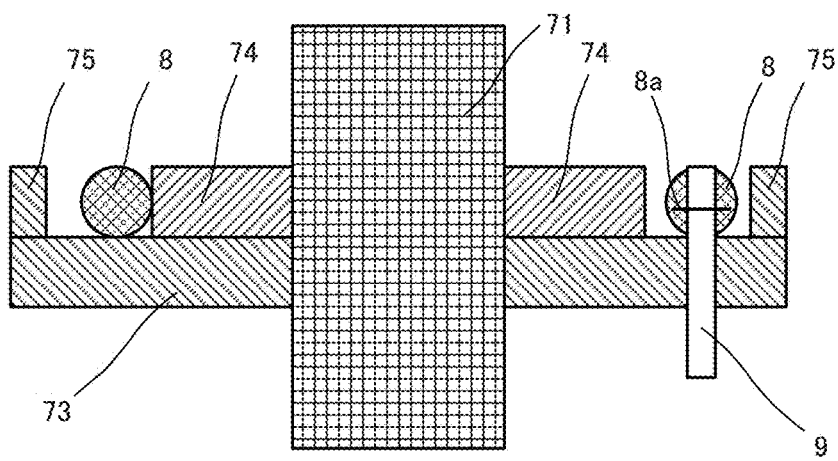

FIGS. 7A and 7B are illustrative of how to assemble the wire 5, rotary unit 7 and elastic unit 8 into the manipulator 1 according to the embodiment described here: FIG. 7A is a plan view of the rotary unit 7 and FIG. 7B is a sectional view of FIG. 7A as taken on line A-A.

In the example of FIGS. 7A and 7B, the elastic unit 8 is provided at both its ends with stops 8a made up of hooks or the like. The stop 8a at one end is locked by a lock portion 77 formed on the disc member 72, and the stop 8a at the other end is joined to the wire 5. When the wire 5, rotary unit 7 and elastic unit 8 are joined together in such a configuration, it is preferable to make use of a temporary fastening pin or member 9 for the purpose of temporary fastening of the stop 8a at the other end during assembling. The temporary fastening member 9 has a structure capable of insertion and extraction through the plate portion 73 of the disc member 72. For instance, the temporary fastening member 9 remains projecting from the plate portion 73 during assembling. Then, the stop 8a at one end of the elastic unit 8 is hooked on the lock portion 77 and the stop 8a at the other end is done on the temporary fastening member 9. The wire 5 may have been connected to the elastic unit 8 or, alternatively, it may be connected to the elastic unit 8 in this state. Thereafter, if the temporary fastening member 9 is pulled out of the plate portion 73, the wire may then get ready for use. The use of such temporary fastening member 9 makes it easy to assemble the wire 5, rotary unit 7 and elastic unit 8 into the manipulator. Note here that the lock portion 77 may have such a structure as shown typically in FIG. 1; the structure of one end of the elastic unit 8 may be modified accordingly.

Figure 8:
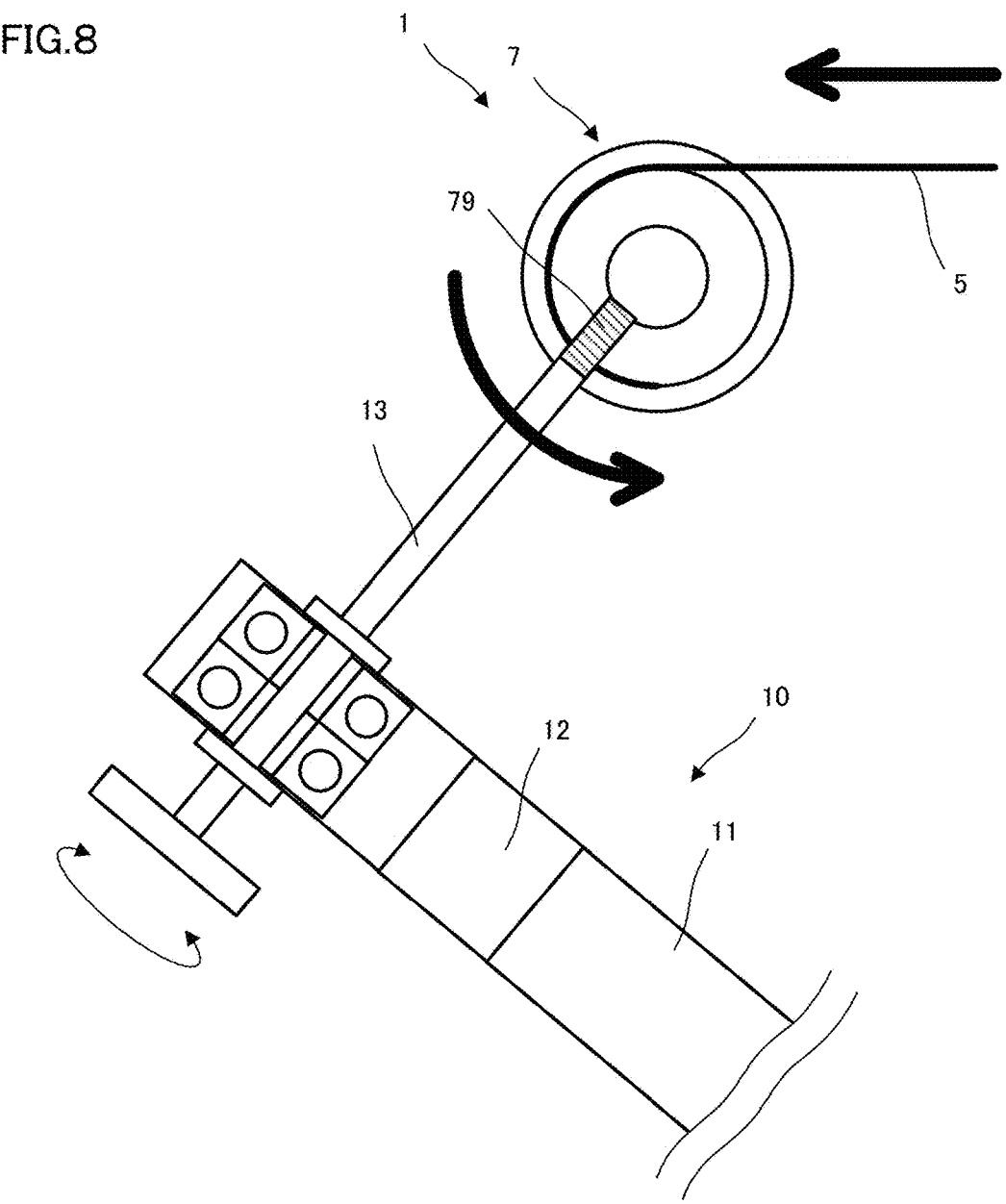
FIG. 8 illustrates one example of how to preset the initial tension in the manipulator described here.

FIG. 8 is illustrative of one example of presetting the initial tension of the manipulator 1 according to the embodiment described here.

A tension adjustor 10 is used to preset the initial tension of the manipulator 1. The tension adjustor 10 includes a handle 11, a load cell 12, and a wrench 13. The handle 11 is used to set the wrench 13 on the rotary unit 7 for rotation. The load cell 12 is adapted to measure a torque on the handle 11 during rotation. The wrench 13 is adapted to rotate a tension-adjustment screw 79 of the rotary unit 7 to fix the disc member 72 to the shaft member 71.

For instance, the handle 11 is first rotated to rotate the disc member 72 of the rotary unit 7 relative to the shaft member 71. Subsequently, the torque measured by the load cell 12 is read out for tension calculation. For tension calculation, use may be made of the following equation. Finally, the wrench 13 may be tightened right at the time when the tension has as optimal value.

$$T = (F \times l)/r$$

where F is a value measured by the load cell 12,
l is a fixed position,
r is a radius of the disc member 72, and
T is a wire tension.

According to the manipulator 1 described here, it is thus possible to preset the initial tension with ease.

Figure 9:
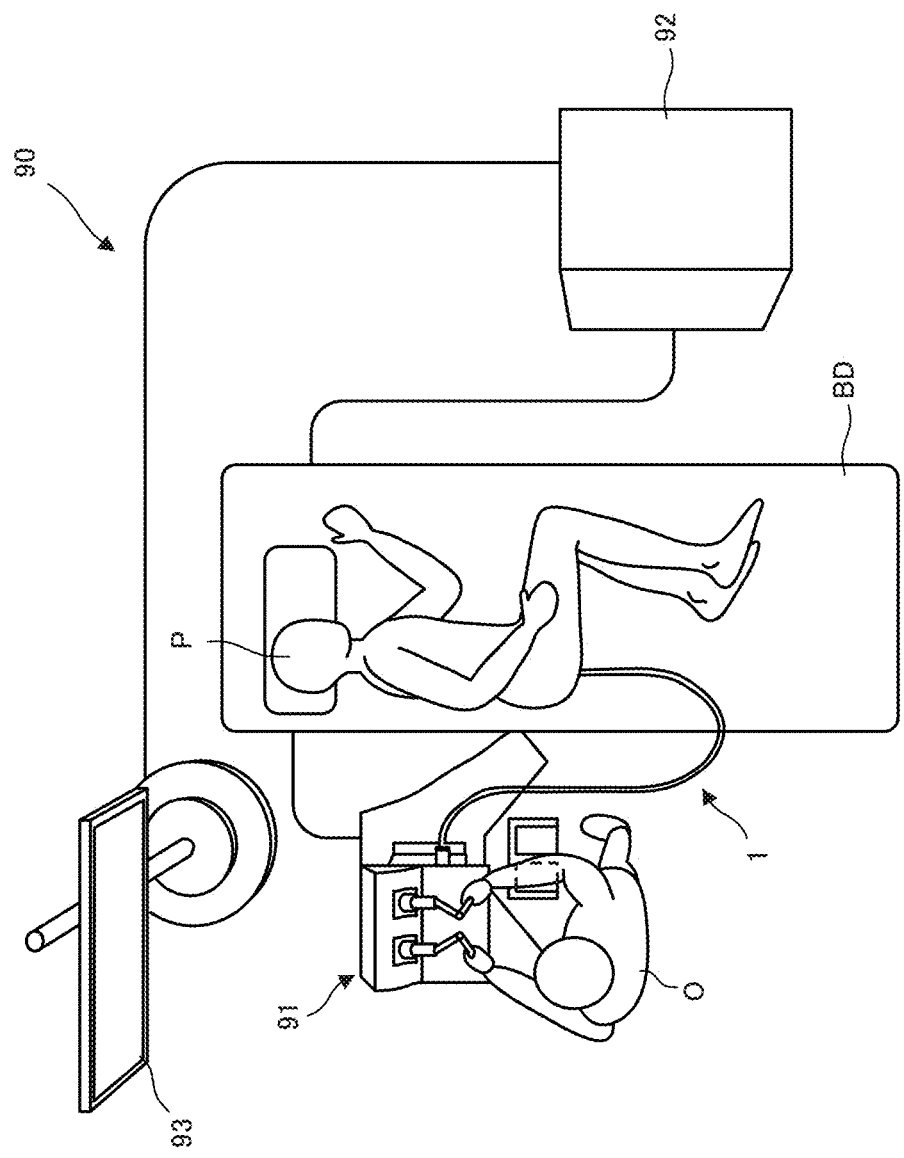
FIG. 9 illustrates the manipulator system to which the manipulator described here is applied.
Figure 10:
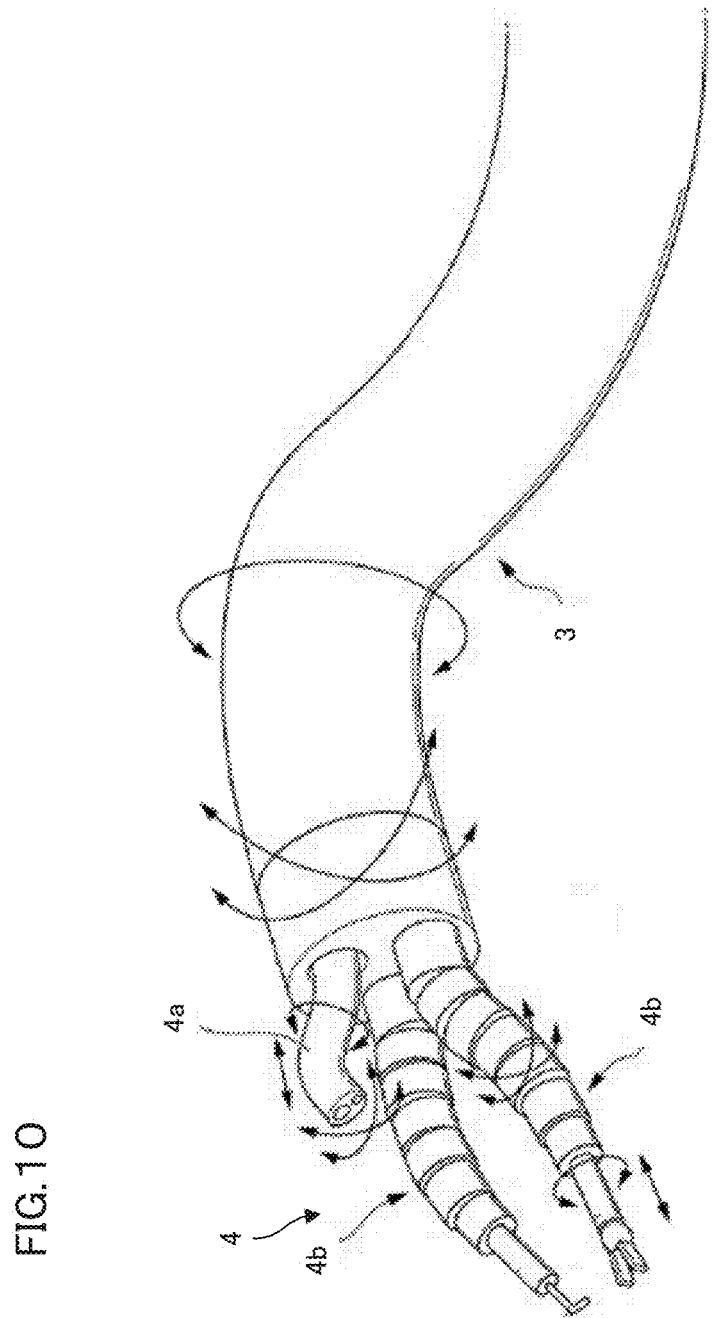
FIG. 10 illustrates one example of the distal end of the manipulator according to the embodiment described here.
Figure 11:
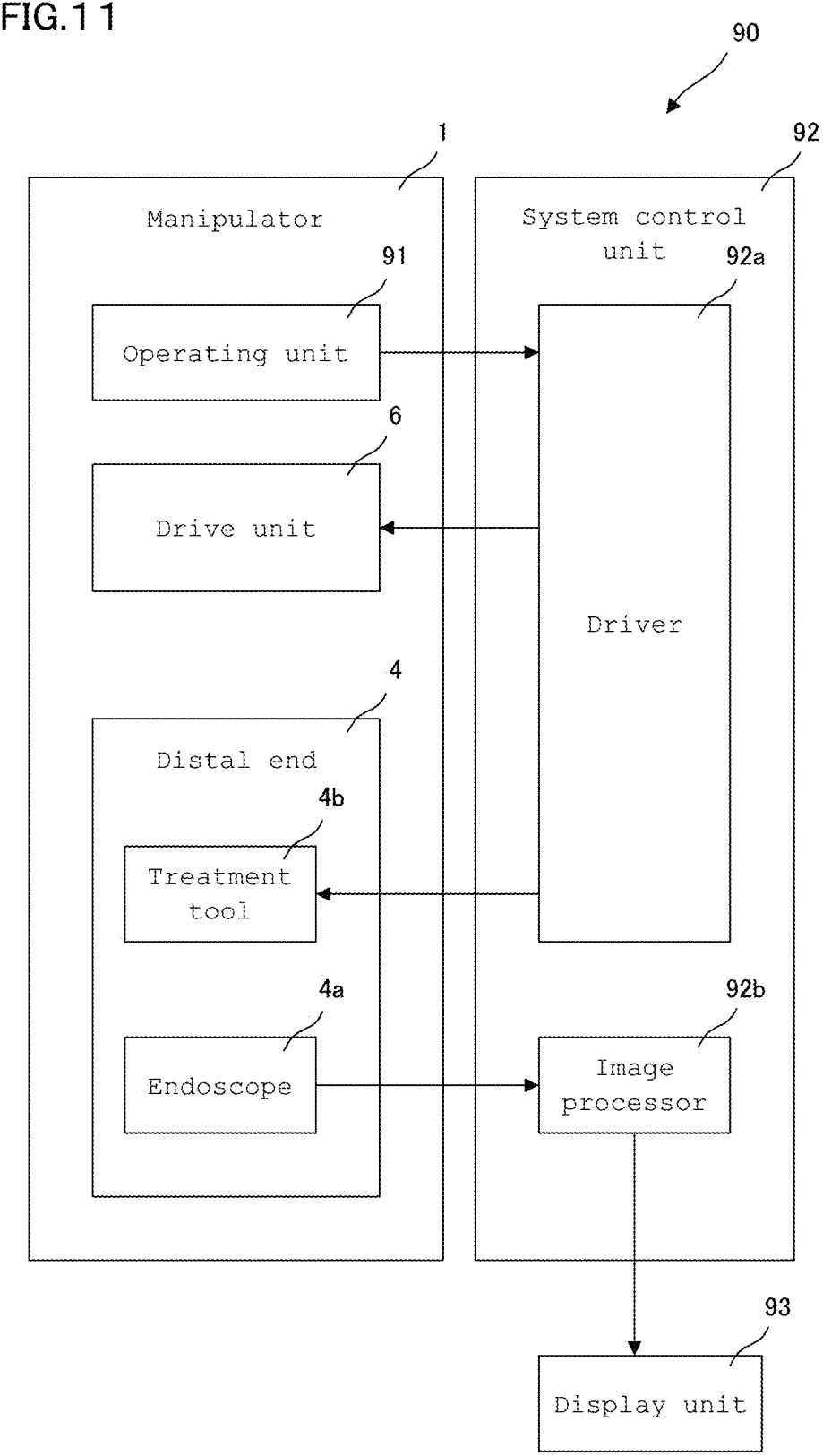
FIG. 11 is illustrative in architecture of the manipulator system to which the manipulator described here is applied.

FIG. 9 shows a manipulator system 90 to which the manipulator 1 described here is applied. FIG. 10 shows one example of the distal end (assembly) 4 of the manipulator 1 described here and FIG. 11 is illustrative in architecture of the manipulator system 90 to which the manipulator 1 described here is applied.

The manipulator system 90 described here has the manipulator 1 of FIG. 1 applied to it. The manipulator system 90 includes an operating unit 91 operated by an operator O, an elongated portion 3 that is capable of insertion through the body cavity of a patient P lying down on an operating table BD, for instance, a soft internal organ such as the large intestine, a manipulator 1 including a distal end 4 or the like of FIG. 1 having an endoscope or the like attached to the distal end of the elongated portion 3, a control unit 92 for control of the manipulator 1 and a display unit 93 for displaying images acquired through the manipulator 1.

As shown in FIG. 9, the operating unit 91 includes a pair of operating handles mounted on a manipulating base, a footswitch located on a floor surface, and so on. The operating unit 91 may have a multi-joint structure. The operating unit 91 is mechanically connected to the elongated portion 3 and distal end 4 for bending operation of the elongated portion 3. The angle of the operating unit 91 in operation is acquired from an angle acquisition device such as an encoder, and the control unit 92 puts the distal end 4 into operation by way of a driver 92a in response to the acquired signal.

As shown in FIG. 10, the manipulator 1 could be an endoscope 4a and a bending or flexing treatment tool 4b working as the distal end assembly 4 or, alternatively, a bending guide tube through which a conventional joint-free treatment tool is inserted. The endoscope 4a includes a viewing/lighting optical system and an imaging device for lighting the interior of the body to obtain images, and such like. Images obtained by the imaging device via the viewing optical system are sent out to the image processor 92b in the control unit 92, where the images are processed and displayed on the display unit 93. While viewing the images displayed on the display unit 93, the operator O puts the manipulator 1 into operation.

According to such manipulator system 90, it is possible to adjust the initial tension of the wire 5 easily yet unerringly during assembling of the manipulator 1.

The manipulator 1 described here includes a main unit 2, an elongated portion 3 that extends from the main unit 2, a distal end 4 that is connected to the elongated portion 3, a wire 5 for transmission of power for putting the distal end 4 into actuation, a drive unit 6 for generation of power to the wire 5, a rotary unit 7 which is located in the main unit 2, around which the wire 5 is wound and which is rotated by the drive unit 6, and a elastic unit 8 that connects the wire 5 to the rotary unit 7. It is thus possible to adjust the initial tension of the wire 5 easily yet unerringly during assembling.

According to the manipulator 1 described here, the rotary unit 7 includes a shaft member 71 that is rotated by the drive unit 6 and a disc member 72 that is attached to the outer periphery of the shaft member 71 and has a peripheral wall. It is thus possible to allow for unerring adjustment in a simple configuration.

According to the manipulator 1 described here, the wire 5 is located along the outer peripheral surfaces 74a and 75a of peripheral walls 74 and 75 and connected at its end to the other end of the elastic unit 8, and the elastic unit 8 is located along the outer peripheral surfaces 74a and 75a of the peripheral walls 74 and 75 and locked at one end to the lock portion 77. It is thus possible to make use of a simple configuration thereby allowing for unerring adjustment of the initial tension of the wire 5 during assembling.

The disc member 72 includes a disc-like plate portion 73, an inner peripheral wall 74 standing upright on the inner peripheral side of the plate portion 73, a columnar projection 76 at least a portion of which is located on the plate portion 73 and a lock portion 77 for fixing one end of the elastic unit 8 in place. It is thus possible to make use of a simple configuration thereby allowing for unerring adjustment of the initial tension of the wire 5 during assembling.

According to the manipulator 1 described here, the rotary unit 7 includes an outer peripheral wall 75 standing upright on the outer periphery of the plate portion 73, the wire 5 is wound around the outer peripheral surface 75b of the outer peripheral wall 75, inserted into a gap 75a formed in the outer peripheral wall 75, wound around the projection 76, located along the outer peripheral surface 74a of the inner peripheral wall 74 and attached at the end to one end of the elastic unit 8, and the elastic unit 8 is located along the outer peripheral surface 74a of the inner peripheral wall 74 is locked at the other end to the lock portion 77. It is thus possible to make use of a simple configuration thereby allowing for unerring adjustment of the initial tension of the wire 5 during assembling.

According to the manipulator 1 described here, a portion of the rotary unit includes a guide for guidance of the wire. It is thus possible to put the wire 5 into smooth actuation.

According to the manipulator 1 described here, the projection 76 includes a guide 76a for guidance of the wire 5. It is thus possible to put the wire 5 into smooth actuation.

According to the manipulator 1 described here, the inner wall 74 includes on its outer peripheral surface 74a a guide 74b for guidance of the wire 5. It is thus possible to put the wire 5 into smooth actuation.

According to the manipulator 1 described here, the rotary unit 7 includes a support portion 78 for supporting the disc member 72 from above and below in a sandwiched manner, and the support portion 78 includes a split member 78a looking as if an annular member were split into two with the shaft member 71 as center and a bolt 78b for joining the split member 78a together. It is thus possible to support the disc member 72 unerringly.

According to the manipulator 1 described here, the rotary unit 7 includes a temporary fastening member 9 for temporary fastening of the juncture of the elastic unit 8 and the wire 5, and the temporary fastening member 9 is provided for insertion and extraction through the disc member 72. It is thus possible to easily assemble the wire 5, rotary unit 7 and elastic unit 8 into the manipulator.

The manipulator system 90 according to one embodiment includes a manipulator 1 that is a guide tube (not shown) through which a treatment tool 4b having a bending or flexing joint assembly or a joint-free treatment tool (not shown) is inserted, an operating unit 91 that puts the manipulator 1 into operation, an image processor 92b that applies image processing to an image signal obtained from an endoscope 4a, and a display unit 93 for displaying image signals transmitted from the image processor 92b. It is thus possible to adjust the initial tension of the wire 5 easily yet unerringly during assembling of the manipulator 1. Note here that the invention may be applied not only to the treatment tools or guide tubes but also to the drive mechanism for endoscopes 4a.

It is here to be appreciated that the invention is in no sense limited to such embodiments as described above. While the explanation of some embodiments embraces numerous specific details for illustration, it would be obvious to those skilled in the art that diverse variations or modifications made thereto are included within the scope of the invention. In other words, illustrative embodiments of the invention are described without excluding generality from the claimed inventions and imposing any limitation thereon.

REFERENCE SIGNS LIST

1: Manipulator
2: Main unit
3: Elongated portion
4: Distal end
5: Wire
6: Drive unit
7: Rotary unit
71: Shaft member
72: Disc member
73: Plate portion
74: Inner peripheral wall
75: Outer peripheral wall
76: Projection
77: Lock portion
78: Support portion
79: Tension-adjustment screw
8: Elastic unit
9: Temporary fastening member

The invention claimed is:

1. A manipulator comprising:
 a main unit provided on a proximal end of the manipulator;
 an elongated portion configured to extend from the main unit;
 a distal end of the elongated portion, the distal end configured to bend or flex with respect to the elongated portion;
 a wire coupled to the main unit and the distal end;
 wherein the main unit comprises:
 a drive unit configured to generate driving power to bend or flex the distal end,
 a rotary unit comprising:
 a shaft member configured to be rotated by the driving power,
 a disc member mounted on an outer periphery of the shaft member, and
 a peripheral wall mounted on the disc member along the circumference of the disc member,
 an elastic unit located along an outer peripheral surface of the peripheral wall,
 a first lock portion configured to lock one end of the elastic unit to the rotary unit, and wherein the wire connects the elastic portion and is wound along the peripheral wall, and the wire is configured to transmit the driving power.

2. The manipulator according to claim 1, wherein the disc member comprises:
 a disc-like plate portion,
 an inner peripheral wall configured to stand upright on an inner peripheral side of the plate portion,
 a columnar projection at least a portion of which is provided to the plate portion, and
 a second lock portion configured to lock another end of the elastic unit.

3. The manipulator according to claim 2, wherein:
 the rotary unit comprises an outer peripheral wall configured to stand upright on the outer periphery of the plate portion,
 the wire is wound around the outer peripheral surface of the outer peripheral wall, inserted into a gap formed in the outer peripheral wall, wound around the projection, located along the outer peripheral surface of the inner peripheral wall and attached at the end to one end of the elastic unit, and
 the elastic unit is located along the outer peripheral surface of the inner peripheral wall and locked at the other end to the second lock portion.

4. The manipulator according to claim 2, wherein the projection comprises a guide for guidance of the wire.

5. The manipulator according to claim 2, wherein the peripheral wall or the inner peripheral wall comprises on its outer peripheral surface a guide for guidance of the wire.

6. The manipulator according to claim 1, wherein a portion of the rotary unit comprises a guide for guidance of the wire.

7. The manipulator according to claim 1, wherein the rotary unit comprises a support portion configured to support the disc member from above and below in a sandwiched manner, and the support portion comprises a two-split member configured to split into two with the shaft member as center and a bolt configured to join the two-split member together.

8. The manipulator according to claim 1, wherein the rotary unit comprises a temporary fastening member configured to fasten a juncture of the elastic unit and the wire, and the temporary fastening member is configured to be inserted and configured to be extracted through the disc member.

9. A manipulator system comprising:
 a manipulator according to claim 1,
 an operating unit configured to be operated by an operator to operate the manipulator,
 a system control unit comprising one or more processors, wherein the one or more processors are configured to:
 obtain an image signal from an endoscope; and
 transmit the image signal to a display.

* * * * *